United States Patent
Bodmer et al.

(10) Patent No.: US 6,623,753 B1
(45) Date of Patent: Sep. 23, 2003

(54) ALLYLAMINE-CONTAINING LIPOSOMES

(75) Inventors: David Bodmer, Klingnau (CH); Thomas Kissel, Staufen (DE); Friedrich Richter, Schönbühl (CH); Harry Tiemessen, Binningen (CH)

(73) Assignee: Novartis AG, Basel (CH)

(*) Notice: Subject to any disclaimer, the term of this patent is extended or adjusted under 35 U.S.C. 154(b) by 1527 days.

(21) Appl. No.: 08/881,216

(22) Filed: Jun. 24, 1997

Related U.S. Application Data

(63) Continuation of application No. 08/628,359, filed on Apr. 5, 1996, now abandoned, which is a continuation of application No. 08/476,147, filed on Jun. 7, 1995, now abandoned, which is a continuation of application No. 07/890,498, filed on May 28, 1992, now abandoned.

(30) Foreign Application Priority Data

May 30, 1991 (GB) ............................................... 9111611

(51) Int. Cl.[7] ............................................... A61K 9/127
(52) U.S. Cl. ............................................... 424/450; 424/43
(58) Field of Search ............................... 424/450, 43–45

(56) References Cited

U.S. PATENT DOCUMENTS

| | | | |
|---|---|---|---|
| 4,755,534 A | | 7/1988 | Stuetz .................. 514/655 |
| 4,812,312 A | * | 3/1989 | Lopez-Berestein et al. . 424/417 |
| 4,891,208 A | * | 1/1990 | Janoff et al. .................. 424/1.1 |
| 5,013,556 A | * | 5/1991 | Woodle et al. .............. 424/450 |
| 5,049,388 A | | 9/1991 | Knight et al. |

FOREIGN PATENT DOCUMENTS

| | | |
|---|---|---|
| GB | 2148711 | 6/1986 |
| WO | WO8603938 | 7/1986 |
| WO | 8603958 | * 7/1986 |
| WO | WO8702219 | 4/1987 |
| WO | WO8707530 | 12/1987 |

OTHER PUBLICATIONS

Birnbaum J. Amer. Acad. Dermatil. 23, # 4 p 782–785, 1990.*
T.C. Jones, Journal of Dermatological Treatment 1, Suppl. 2, pp. 29–32 (1990).
J.E. Birnbaum, Journal of American Academy of Dermatology, vol. 23, (No. 4/Part 2, Suppl.) pp. 782–785 (1990).
F. Szoka, Ann. Rev. Biophys. Bioeng. 9, pp. 467–508, 1980.
J.C. Jensen, Clin. and Exper. Derm., vol. 14, pp. 110–113 (1989).

* cited by examiner

*Primary Examiner*—Gollamudi S. Kishore
(74) *Attorney, Agent, or Firm*—Gabriel Lopez

(57) ABSTRACT

The invention concerns liposomal preparations comprising as the active agent a compound of formula I

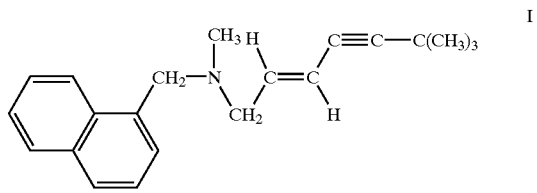

in free base form or in acid addition salt form. It also concerns a method of preparation of such liposomal preparations by encapsulating a compound of formula I with an appropriate liposome forming material, a corresponding pharmaceutical compositions, and methods of treatment of systemic, topical and pulmonal fungal infections.

1 Claim, 4 Drawing Sheets

POPC                                                        Compound 1

ALLYLAMINE-CONTAINING LIPOSOMES

This is a continuation of application Ser. No. 08/628,359 filed Apr. 5, 1996 now abandoned, which is a continuation of application Ser. No. 08/476,147 filed Jun. 7, 1995, now abandoned, which is a continuation of application Ser. No. 07/890,498 filed May 28, 1992, now abandoned.

This invention relates to allylamine-containing liposomes, i.e. liposomes loaded with an allylamine compound as the pharmacologically active agent.

The present invention provides in an aspect liposomes comprising a compound of formula I

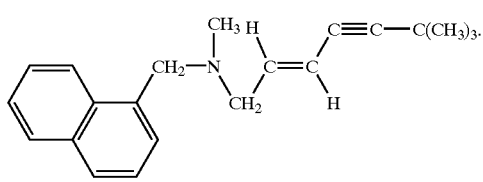

The compound of formula I may be used e.g. in free form or in acid addition salt form. An acid addition salt form may be prepared from the free base form in conventional manner and vice-versa. Examples of suitable acid addition salt forms are the hydrochloride, the lactate and the ascorbate.

The compound of formula I is known from e.g. BE-PS-853'976 and EP-A-24'587. It belongs to the class of allylamine anti-mycotics. It is acknowledged in the art under its generic name terbinafine and is commercially available under the tradename LAMISIL. While terbinafine is highly active upon both topical and oral administration, in vitro serum can antagonize to some extent its antifungal activity.

It is thus desirable to find a drug delivery system which can improve the bioavailability of the compound of formula I in order to overcome serum binding and/or favourably influence parameters such as pharmacokinetics and tissue distribution and/or reduce side effects and toxicity. Reduction of side effects and toxicity with maintenance or increase in the activity and therapeutic efficacy of the drug substance is pursued.

A promising approach meeting the above-mentioned criteria has now been found in the form of liposomes comprising the compound of formula I as the active agent. Thus pharmaceutically acceptable e.g. parenteral dosage form for the lipophilic compound of formula I has been obtained by means of liposomal preparations. No surface active agents (tensides) are required thereby and additional side effect problems commonly associated with their use are thus avoided.

A pulmonary application of liposomes comprising the compound of formula I e.g. by metered dose inhaler (MDI), aqueous or powder aerosol may lead to an immediate or sustained release of compound of formula I, depending on the liposomal composition, to produce the antifungal activity. A topical application of liposomes containing the compound of formula I may lead to enhanced accumulation of the drug at the site of administration, in turn leading to enhanced efficacy of the compound of formula I compared to non-liposomal application forms. On pulmonal application the liposomes comprising the compound of formula I are effective against fungal diseases of the lung such as candidiasis and various types of aspergillosis, e.g. infections by *Aspergillus fumigatus* and non-fumigatus Aspergilli.

An application by injection of liposomes according to the invention may lead to improved efficacy of the active agent in comparison to the same amount of the same agent when injected in a conventional injectable form. On the other hand equivalent efficacy of the compound of formula I may be achieved with a smaller amount of the active agent, when administered in form of liposomes carrying the compound of formula I. A substantial reduction of the required amount of the compound of formula I for treating a fungal disease may be achieved in this way.

Liposomes are lipid vesicles which are formed on addition of an aqueous solution to a dry film of phospholipids, e.g. if necessary with the addition of energy, or even to a certain extent spontaneously. The lipid most widely used is phosphatidylcholine. Altering the lipid composition, size, charge and membrane fluidity of the liposomes can greatly influence their distribution in the body. Drug molecules can either be encapsulated in the aqueous space or intercalated into the bilayer. In the last two decades liposomes have been applied to a variety of drugs but also to genetic material, enzymes and other (macro)molecules as delivery vehicles into living cells and other hydrophobic barriers in pharmacology, medicine, genetic engineering and in the cosmetic and food industries. In the treatment of systemic fungal infections these vesicles have also been successfully used as carriers of Amphotericin B and of nystatine.

| Abbreviations | |
|---|---|
| AMB | Amphotericin-B |
| DMPC | Dimyristoyl-phosphatidyl-choline |
| DMPG | Dimyristoyl-phosphatidyl-glycerol |
| DOPC | Dioleoyl-phosphatidyl-choline |
| DOPG | Dioleoyl-phosphatidyl-glycerol |
| DOPS | Dioleoyl-phosphatidyl-serine |
| DPPC | Dipalmitoyl-phosphatidyl-choline |
| DSPC | Distearoyl-phosphatidyl-choline |
| DSPG | Distearoyl-phosphatidyl-glycerol |
| GPC | Gel permeation chromatography |
| HEPES | Hydroxy ethyl piperazine ethane sulfonic acid |
| HPC | Hydrogenated phosphatidyl choline |
| HPLC | High performance liquid chromatography |
| IR/ATR | Infrared-attenuated total reflection spectoscopy |
| MDI | Metered dose inhaler |
| MLV | Multilamellar vesicle |
| PC | Phosphatidyl-choline |
| PE-PEG | Phosphatidylethanolaminepolyethyleneglycol |
| PG | Phophatidyl-glycerol |
| POPC | Palmitoyl-oleoyl-phosphatidyl-choline |
| POPG | Palmitoyl-oleoyl-phosphatidyl-glycerol |
| PS | Phosphatidyl-serine |
| TC | Phase transition temperature |

BRIEF DESCRIPTION OF THE DRAWINGS

Explanation of the Figures

Figure 1:
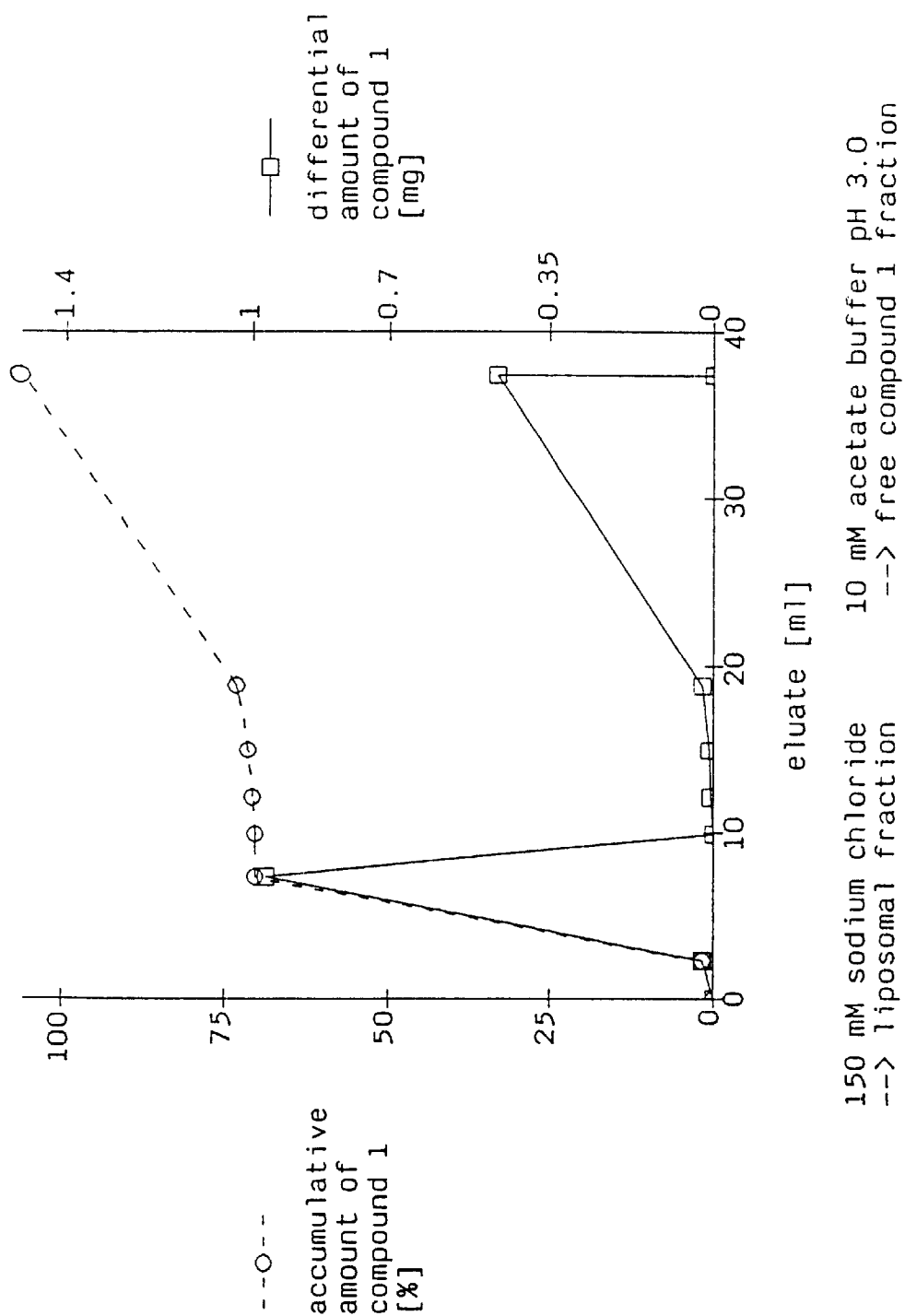

FIG. 1: Elution profile of a mixture of 0.4 mg free compound of formula I and of 1.0 mg liposomes of the invention [see Example 1, a)].

Figure 2:
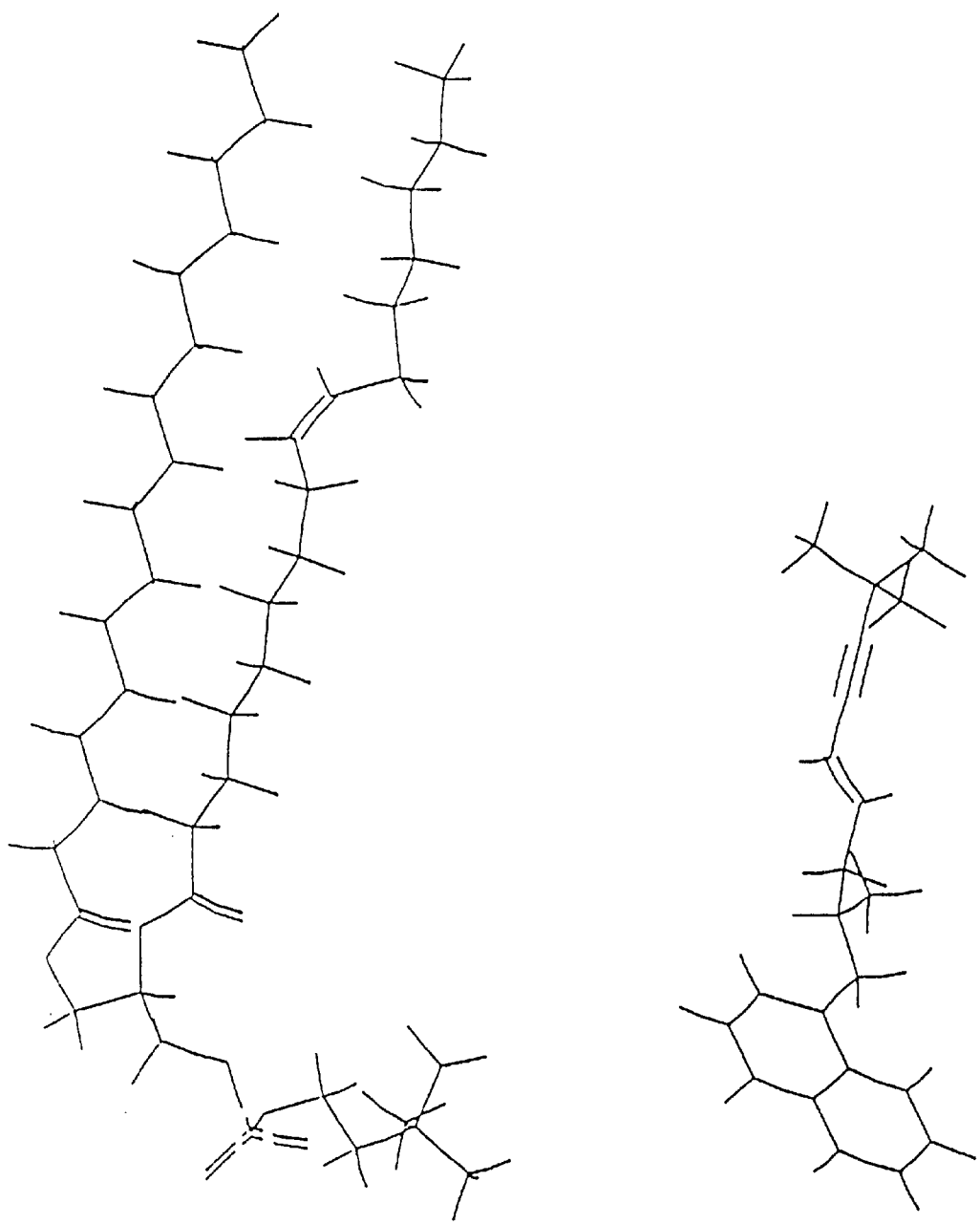

FIG. 2: Computer modelling showing the orientation of compound of formula I and POPC in multi-bilayer membranes [see Example 1, h)].

Figure 3:
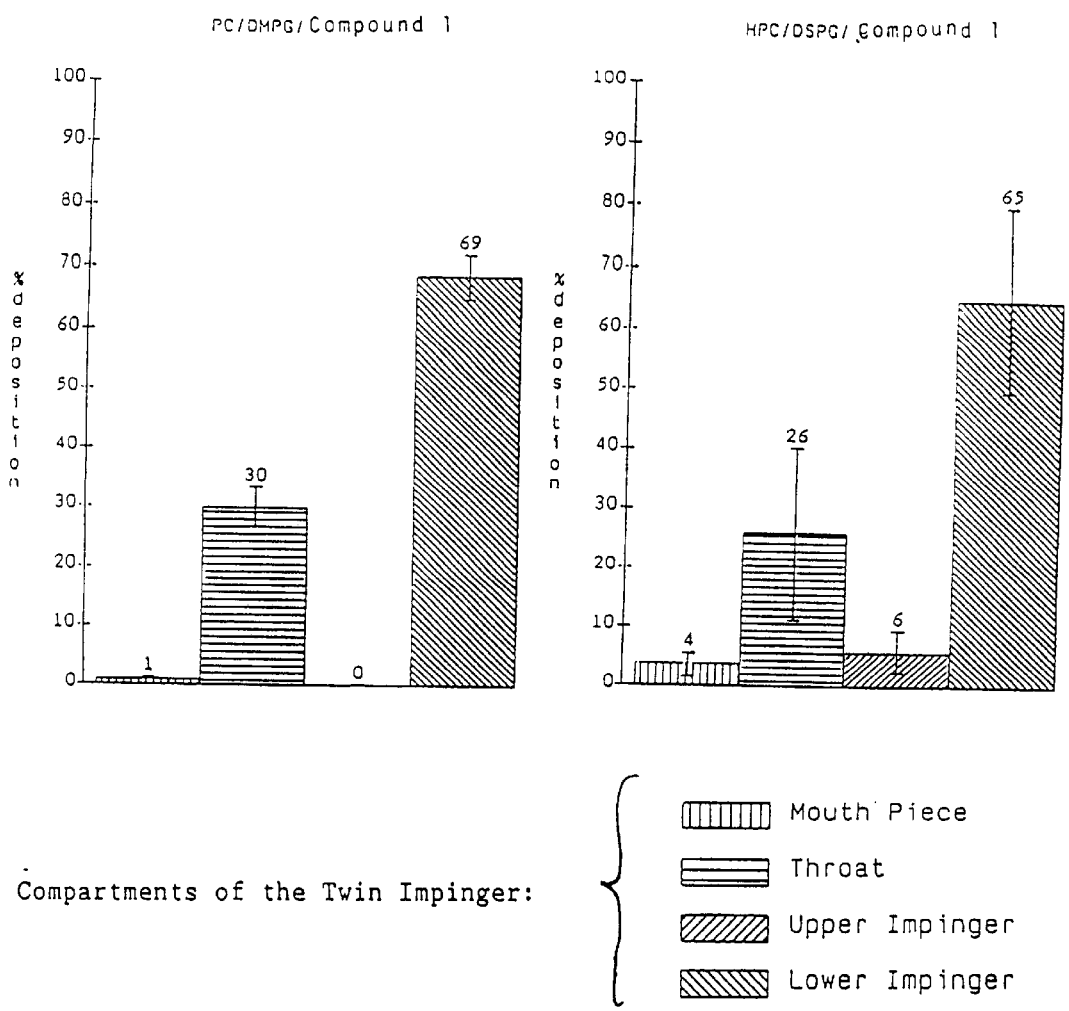

FIG. 3: Deposition of compound of formula I in the various compartments of the Twin Impinger after nebulization of liposomal suspensions.

Figure 4:
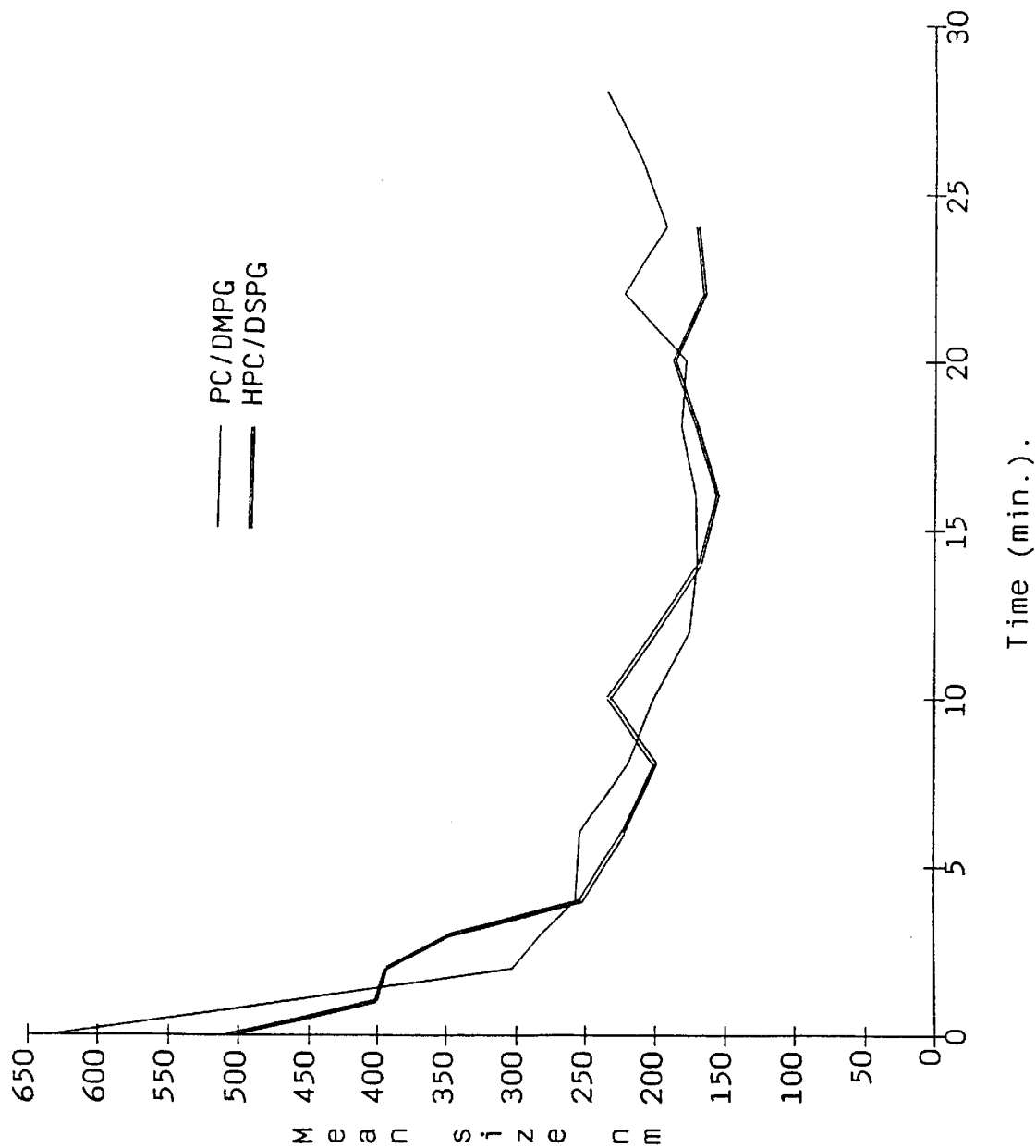

FIG. 4: Particle size of liposomes within the nebulizer.

The liposomes of the invention may be obtained by a process comprising encapsulating a compound of formula I with an appropriate liposome forming material. This process forms another aspect of the invention.

The process of the invention may be effected in conventional manner, e.g. along lines similar to the procedures described in F. Szoka and D. Papahadjopoulos, "Liposomes and their uses in biology and medicine", *Ann. N.Y. Acad. Sci.* 308 (1978) 1–462, in R. L. Juliano & D. Layton, "Liposomes as a drug delivery system" in *Drug Delivery Systems*, Oxford University Press, Inc., New York (1980) p. 189–236, in M. J. Ostro, *Liposomes*, M. Dekker Inc., New York (1983) and in G. Lopez-Berenstein and I. J. Fidler, *Liposomes in the Therapy of Infectious Diseases and Cancer*, A. R. Liss, Inc., New York (1989); R. R. C. New, *Liposomes—a practical approach*, IRL Press, Oxford, New York, Tokyo (1990).

Further references reating to liposomes and their use are: I. W. Kellaway and S. J. Fair, *Adv. Drug Delivery Reviews* 5 [1990] 149, F. Martin, *J. Liposome Res.* 1 [1990] 407, K. Egbaria and N. Weiner, *Adv. Drug Delivery Reviews* 5 (1990) 287, A. Klibanov et al., *FEBS* 268 (1990) 235.

The liposome forming material is essentially a phospholipid or mixture of phospholipids.

The active substance preferably is intercalated and thereafter located in the phospholipid bilayer.

A preferred process variant for liposome formation comprises a) forming a solution of a compound of formula I and a lipid in an organic solvent, b) removing the solvent from the solution to give a residue, c) suspending the residue in a solution of a buffer, d) subjecting the suspension to agitation and homogenization until liposomes are produced, and e) isolating the liposomes.

In step a) the term "solution" covers "pseudo" solutions like emulsions; however, it is preferred to produce a uniform, clear solution. Any solvent system may be used which will dissolve or solubilize the compound of formula I and the lipid. The system may be a single solvent or a mixture of solvents. It may contain up to e.g. 15% water. If desired a surfactant may be present. The solvent system may comprise any appropriate organic solvent which can be removed from the lipid by evaporation. A wide variety of ethers such as diethyl ether and diisopropyl ether, esters such as ethyl acetate, alcohols such as methanol, ethanol and tert-butanol, and halogenated hydrocarbons such as methylene chloride and chloroform may be used. If desired acetic acid may be present. It is preferred to use methylene chloride, methanol or tert-butanol.

In step b) the solvent may be removed by many conventional means. Preferred means comprise evaporation under a low vacuum, e.g. 10 to 50 mm Hg, or freeze-drying under a high vacuum, e.g. at below 5 mm Hg, e.g. 0.1 mm Hg. One may also increase the surface of the dry lipid while keeping the volume of both the solvent and the aqueous buffer (step c) down. Such increase of the lipid surface can be obtained by drying the lipids down on a finely divided support (such as crystals of sodium chloride, lactose or other polysaccharides) or by drying the lipids down on glass beads (R. R. C. New, *Liposomes—a practical approach*, IRL Press, Oxford, New York, Tokyo (1990)). When using the freeze-drying method the step is suitably effected at a temperature below room temperature, and the vacuum and temperature controlled such that the mixture being evaporated is about 1–3° C. cooler than the surroundings. Such control may be effected in conventional manner. A typical program for freeze-drying starts at about −60° C. and increases to −15° C. over 12 hours. The temperature is then increases to +10° C. and maintained for 2 hours. An alternative way to remove the solvent in technical scale production of liposomes is the spray-drying method as described e.g. by H. Kikuchi et al., *Chem. Pharm. Bull.* 35, 1522 (1991). According to this method the lipids and the drug are dissolved in the volatile organic solvent in which a core material can be suspended, e.g. sodium chloride or a saccharose. The obtained solution or suspension is then spray-dried in a conventional way e.g. in a Büchi 190 Mini Spay Dryer.

In step c) the buffer used is preferably a phosphate buffer, e.g. of pH 4–8, e.g. of pH 5–6.8. Preferably the aqueous phase is hypotonic, e.g. less than 300 mosmol/liter. The resultant suspension preferably contains about 0.001 to about 0.2 g lipid per ml.

In step d) preferably mechanical treatment is used, e.g. by vortexing or by means of a homogenizer such as Superdispax (IKA Labor-technik, Staufen, Germany) or a Microfluidizer (Microfluidics Corp., Newton, Mass., USA). Homogenization may also be provided by ultrasonic radiation. Suitable frequencies of such radiation may be for example from 30 to 80 kHz. A typical power is from 200 to 400 watts for about 10 ml of mixture being homogenized or agitated. Naturally it is preferred to have the mixture being homogenized separated from any titanium or other metal associated with the ultrasonic radiation generator to avoid contamination by the metal. The temperature is preferably from about 10° to about 70° C. Room temperature is preferred for unsaturated lipids and 60°–70° C. for saturated lipids. If desired the ultrasonic radiation may be followed by agitation by a high speed mechanical stirrer at e.g. 10000 to 27000 rpm.

In step e) the liposomes may be isolated according to conventional techniques, e.g. by ultrafiltration, centrifugation, ion-exchange or gel chromatography, dialysis etc. Isolation of the vesicles is not necessary if the drug substance is incorporated to a high extent into the phospholipid bilayer. This is the case e.g. with concentrations of compound 1 below 1 mg/ml. The liposomes may be filtered and sterilized through a filter with suitably small openings, e.g. 0.1 to 1 micron. If desired the filtration may be effected above the phase transition point of the lipid, e.g. from 30° to 70° C. In order to improve long term stability the preparations are subjected to freeze drying.

In another aspect the invention provides a composition comprising a compound of formula I in association with a phospholipid. These are especially useful for forming liposomes e.g. as described in e.g. step a) above.

A further, preferred, single-step liposomal preparation method for large-scale preparation of liposomes containing the compound of formula I is as described by M. Brandl et al. in *Drug Development and Industrial Pharmacy* 16 (1990) 2167, according to which the phospholipids and the drug are dispersed directly in the aqueous phase followed by homogenization, e.g. in a suitable homogenizer e.g. commercially available under the tradename Microfluidizer.

The vesicles formed may be unilamellar or multilamellar. Their size may vary from about 20 nm to about 10 $\mu$m in mean diameter. They preferably are less than about 200 nm in diameter. The compound of formula I is preferably part of the phospholipid lamellae: only minor amounts are part of the intraliposomal fluid or both. Incorporation into the phospholipid bilayers can be up to a concentration of at least 1 mg/ml. The liposomes comprise one or more lipids, preferably phospholipids, e.g. phosphomonoglyceride, phosphatidic acid and sphingolipid, preferably phosphatidylcholine, phosphatidylserine, phosphatidylglycerol, sphingomyelin, phosphatidylethanolamine, stearylamine or phosphatidic acid; especially dimyristoylphosphatidylcholine, dimyristoylphosphatidylglycerol, distearoylphosphatidylcholine, distearoylphosphatidylglycerol, phosphatidylcholine, phosphatidylglycerol and phosphatidylserine. The liposomes may comprise a sterol such as cholesterol.

Further, phosphatidylethanolaminepolyethyleneglycol (PE-PEG) can be incorporated into the liposomes and may increase the plasma half-life of the liposome after i.v. application, resulting in a sustained release of compound of formula I or in targeted delivery of compound of formula I by the liposomes. For injection purposes hydrogenated phospholipids having a melting point above 42° C. are preferred, e.g. DSPC, DSPG, or HPC.

The total concentration of phospholipids is from about 1 mg/ml to about 200 mg/ml, it preferably is between 15 mg/ml and 100 mg/ml. The concentration of compound of formula I is e.g. from about 0.1 mg/ml to about 20 mg/ml, it preferably is from about 0.3 mg/ml to about 10 mg/ml, especially about 5 mg/ml. The weight ratio of the compound of formula I to the total phospholipids is e.g. from about 1:1 to about 1:2000, preferably about 1:10. The liposomes may be isolated and sterilized in conventional manner.

Further synthetic phospholipids which can advantageously be used are synthetic phospholipids such as phosphatidylethanolamine-polyethylene glycol (PE-PEG) which, particularly when introduced in neutral and small liposomes, result in increased plasma half-life.

Some liposomes constituted by neutral, i.e. uncharged phospholipids, may exhibit a degree of instability, such as aggregation and sedimentation after storage for several days. This may be prevented by lyophilization of liposomes and by their re-suspension shortly before use. It is indicated to cool the liposomes rapidly to below the eutectic temperature, e.g. to –28° C., preferably to –40° C., within 30 minutes if lactose is used as a cryoprotectant to get homogenous products. Indicated cryoprotectants are e.g. sucrose, trehalose, lactose, mannitol, maltose, fructose, glucose, galactose, mannose, xylit and sorbit, preferably lactose, maltose, sucrose and trehalose, especially lactose and maltose, particularly lactose 9%. During lyophilization a decrease in diameter of about 10% to 40% may take place. Generally no significant change of size and content occurs after lyophilization during the first two weeks of storage at 5° C. After one month a 15% reduction of vesicle size may be observed in some liposomes. The concentration of cryoprotectant is not crucial and is in the range of from about 2% to about 10%. Storage is preferably effected at around 5° C.

The osmolarity of the liposomes after reconstitution is well-suited for e.g. parenteral application and typically is from about 250 to about 500, e.g. 290 to 350 mosmol/l.

Reconstitution is effected by adding water to obtain the original volume. Preferably this is effected shortly before use. For analytical determination of the compound of formula I and of the phospholipids, an aqueous reconstituted sample preferably is diluted 1:1 with an alcohol such as methanol 50%.

Sterilization may be achieved by sterile filtration (0.2 μm pore size) of the liposomes prior to aseptic filling and freeze drying. For large scale preparation it is prefered to use 1% of benzylalcohol as a preservative during processing in the aqueous phase. Benzylalcohol may be completely removed again during the final freeze drying step.

Surprisingly a compound of formula I when incorporated in the lipid membrane usually is protonated even when liposomes is effected starting from the free base.

The following Examples illustrate the invention (the compound of formula I is hereafter briefly named Compound 1):

EXAMPLE 1

Preparation of Liposomes
(Compound 1; Small Scale)

10 mg of the compound 1 in free base form is solubilized in methanol and mixed with methanolic solutions of soybean phosphatidyl-choline (PC) and dimyristoyl-phosphatidyl-glycerol (DMPG) in a molar ratio of 1:4:2, i.e. a weight/weight ratio of 1:7:3, respectively. The mixture is dried in a round-bottom flask under vacuum using a rotary evaporator to form a lipid/compound 1 film. The dried film is hydrated by shaking with 10 ml of 20 mM phosphate buffer pH 6.8 containing 9% of the cryoprotectant lactose. The liposomes which form are multilamellar vesicles (MLV's) having heterogeneous sizes up to about 50 microns. The MLV suspension is homogenized by vortexing and sized by sequential extrusion twice through nucleopore polycarbonate membranes with 1, 0.4 and 0.2 micron pore sizes. Subsequently the liposomal preparation is lyophilized and the isolated liposomes are stored at 5° C.

In variants of Example 1 maltose, sucrose or, respectively, trehalose is used as the cryoprotectant substance.

In a further variant homogenization of the MLV's is effected by ultrasound treatment.

In a further variant homogenization of the MLV's is effected by treatment with a Superdispax homogenizer (IKA Labortechnik, Staufen, Germany).

In a further variant homogenization of the MLV's is effected by treatment with a Microfluidizer homogenizer (Microfluidics Corp., Newton, Mass., USA).

In further variants soy-bean PC and DMPG are replaced by the following phospholipids:
dimyristoyl-PC (DMPC);
dipalmitoyl-PC (DPPC);
dioleoyl-PC (DOPC);
dioleoyl-PG (DOPG);
palmitoyl-oleyl-PC (POPC);
palmitoyl-oleoyl-PG (POPG);
dioleoyl-phosphatidyl-serine (DOPS);
phosphatidyl-serine (PS) from bovine brain; and
phosphatidylethanolaminepolyethyleneglycol (PE-PEG)

In a further variant the compound of formula I in hydrochloric acid addition salt form is used.

TABLE 1

Examples of liposomes of compound 1:

| Batch No. | Compound 1 [mg/ml] | Phospholipids Ratio [w/w] | Concentration [mg/ml] | Ratio (molar) [compound/phospholipids] | Vesicle size* (nm) |
|---|---|---|---|---|---|
| 1 | 1 (base) | PC/DMPG 7/3 | 15 | 1/6 | 215 |
| 2 | 1 (HCl-salt) | PC/DMPC 7/3 | 15 | 1/6 | 223 |
| 3 | 0.3–3.0 (base) | PC/DMPG 7/3 | 15 | 1/2–1/20 | |
| 4 | 1 (base) | POPC/DOPS 7/3 | 15 | 1/6 | 240 |
| 5 | 3 (base) | POPC/DOPS 7/3 | 30 | 1/4 | 171 |
| 6 | 3 (base) | POPC/DOPS 7/3 | 30 | 1/4 | 250 |
| 7 | 3 (base) | POPC/DOPS 7/3 | 30 | 1/4 | 250 |

*as hydrodynamic parameter

Characterization a) Maximal Encapsulation Capacity

The liposomal preparations are suspensions of small vesicles (size between 100–250 nm in diameter) with a milky appearance which are stable in the fluid state for several days.

In order to assess the amount of compound of formula I which is encapsulated in the vesicles samples are subjected to GPC using either 10 ml of Sephadex G25 filled into glass columns or prepacked ready to use pd10 columns (Pharmacia) with 9.1 ml Sephadex G25. All columns are washed before use with eluent three times the void volume of the column.

Compound 1 liposomes were prepared as described above using soy-bean phosphatidylcholine and dimyristoyl-phosphatidyl-glycerol (DMPG) in a total concentration of 15 mg/ml, ratio 7:3. Analytical samples are applied to a gel permeation chromatography (GPC) column and assayed for liposomally encapsulated compound 1 and for free compound 1:

TABLE 2

Incorporation capacity of liposomes for compound 1 with different buffers

| Concentration (mg/ml) | | Molar ratio[1] | Observation[2] | GPC-fractions (%) | | Vesicle size[3] | | Loss[4] (%) |
|---|---|---|---|---|---|---|---|---|
| theoret. | found | theoret. | of crystals | free | liposomal | d (nm) | pD | found |
| phosphate buffer (20 mM, pH 6.8): | | | | | | | | |
| 1 | 0.93 | 1:6.5 | – | 0 | >91 | 141 | 2 | 5 |
| 1.5 | 1.39 | 1:4.3 | + | <1 | >76 | 149 | 4 | 14 |
| 2 | 1.30 | 1:3.3 | + | 0 | >80 | 143 | 2 | 26 |
| 2.5 | 1.25 | 1:2.6 | + | 0 | 78 | 196 | 6 | 35 |
| 3 | 1.23 | 1:2.2 | + | <1 | 83 | 139 | 2 | 32 |
| HEPES buffer (35 mM, pH 6.8): | | | | | | | | |
| 1 | 0.90 | 1:6.5 | – | 0 | 86 | 131 | 3 | 4 |
| 1.5 | 1.53 | 1:4.3 | (+) | <1 | >80 | 147 | 3 | 6 |
| 2 | 1.50 | 1:3.3 | + | 14 | 52 | 166 | 4 | 17 |
| 2.5 | 1.43 | 1:2.6 | + | <1 | 54 | 161 | 2 | 25 |
| 3 | 2.23 | 1:2.2 | + | >1 | >67 | 147 | 2 | 17 |
| water: | | | | | | | | |
| 1 | 0.99 | 1:6.5 | – | 0 | 82 | 99 | 2 | 5 |
| 1.5 | 1.58 | 1:4.3 | – | 0 | 91 | 121 | 2 | 5 |
| 2 | 1.99 | 1:3.3 | – | 0 | 90 | 131 | 2 | 4 |
| 2.5 | 1.47 | 1:2.6 | – | <1 | 86 | 124 | 3 | 11 |
| 3 | 2.46 | 1:2.2 | (+) | <1 | 83 | 126 | 3 | 10 |

[1] molar ratio of compound 1 to phospholipids
[2] observation by microscopy (Axioskop, Zeiss)
[3] vesicles size: d = diameter, pD = polydispersity (1 = monodispers, 10 = polydispers)
[4] loss = residues on flask and filters after manufacture Samples (1 ml) are applied on the column and the liposomal fraction is eluted with 0.15 M sodium chloride (0.9%) in water. After 10 to 15 ml the eluent is replaced by 10 mM acetate buffer pH 3 in order to elute compound of formula I not encapsulated in the vesicles (free compound 1). The fractions are assayed for compound 1 by HPLC analysis [see i)].

At phospholipid concentrations of 15 mg/ml compound 1 may be fully encapsulated in the vesicles up to concentrations of 1 mg/ml in phosphate buffer pH 6.8. This may be assayed either by visualizing (microscopy) crystals of compound 1 which are formed when drug substance is added in excess or by separation of not encapsulated compound 1 from liposomal compound 1 by means of GPC using Sephadex G25. FIG. 1 displays the elution profile of a mixture of 0.4 mg free compound 1 and 1.0 mg compound 1 liposomes. 100% of the compound of formula I applied on the column is recovered. The liposomal fraction is eluted with 0.9% sodium chloride (12 ml), free compound 1 is eluted with 10 mM acetate buffer ph 3.0. The continuous line represents the amount of compound 1 in the single fractions; the dashed line shows the cumulative amount of eluted compound 1.

The encapsulation capacity is influenced by the buffer compositions used for hydration: with phosphate buffer and HEPES buffer only 1 mg/ml may be encapsulated. It may be observed that compound 1 gets precipitated to some extent by the two buffers. When demineralized water is used incorporation of up to 2.5 mg/ml may be achieved (Table 2):

Liposomal preparations with higher concentrations of compound 1, i.e. 2 and 4 mg/ml, and a variety of phospholipids (Table 3) confirmed the approximate limit of 1 mg compound 1 /ml at phospholipid concentrations of 15 mg/ml i.e. an approximate molar drug/lipid ratio of 1:6. Encapsulation is independent of the various phospholipids used:

TABLE 3

Encapsulation of compound 1 at concentrations of 2 and 4 mg/ml and with various phospholipids

| | Compound 1 concentration (mg/ml) found | |
|---|---|---|
| Phospholipids | 2 mg/ml-theoret. | 4 mg/ml - theoret. |
| PC | 1.0 ± 0.5 | 1.2 ± 0.7 |
| PC/DOPG | 1.8 ± 0.1 | 2.2 ± 1.0 |
| PC/DOPS | 1.6 ± 0.2 | 3.0 ± 0.6 |
| HPC | 2.0 ± 0.2 | 3.5 ± 0.4 |
| HPC/DOPG | 1.7 ± 0.3 | 2.2 ± 0.1 |
| HPC/DOPS | 2.0 ± 0.3 | 3.2 ± 0.6 |
| POPC | 1.8 ± 0.2 | 3.4 ± 0.4 |
| POPC/DOPG | 1.9 ± 0.1 | 2.5 ± 0.3 |
| POPC/DOPS | 1.4 ± 0.2 | 2.8 ± 0.4 |
| DOPC/DOPG | 1.6 ± 0.3 | 3.4 ± 0.4 |
| DMPC | 1.8 ± 0.4 | 1.5 ± 1.0 |
| DMPC/DMPG | 2.0 ± 0.3 | 3.0 ± 1.2 |

Phosphate buffer (20 mM, pH 6.8) was used for hydration. Phospholipid concentration was 15 mg/ml. Compound 1 was determined after filtration through 0.2 µm membranes.

Three preparations of each concentration were examined (mean±SD, n=3).

b) Encapsulation Efficiency

At compound 1 (in free base form) concentrations up to 1 mg/ml content efficiency is more than 90%. At higher concentrations efficiency is reduced due to precipitation of compound 1 in excess (not encapsulated).

c) Yields

Yields are in the 70–80% range at batch size up to 10 ml (10 mg compound 1). At 100 ml (100 mg compound 1) yields are 90% and at 1 l (1 g compound 1) more than 90%.

d) Impurities and Stability

Two lyophilized liposomes variants of compound 1 (compositions: see batches 1 and 2, Table 1) were placed on stability testing at different temperatures and ambient humidity: −25° C., 5° C., 25° C. and 30° C. at 75% relative humidity. Sterilization is achieved by filtration through 0.2 μm membranes and aseptic filling on a sterile bench. Results are summarized in Table 4.

Almost no degradation of compound 1 was detected after manufacture. After one month impurity levels were found to be less than 2% even at 30° C.

The three months stability data show that after 1 month a minor increase in degradation products occurs in particular at elevated temperature. Impurity levels after three months storage at 5° C. were below 1%. Storage at 5° C. is adequate.

TABLE 4

Stability of compound 1 liposomes

| Storage conditions | Compound 1 loading (%) | | Degradation products of compound 1 (%) | |
| --- | --- | --- | --- | --- |
|  | batch 2 | batch 1 | batch 2 | batch 1 |
| initial −25° C. | 100 | 100 | 0.2 | 0.1 |
| 1 month 3 months 5° C. | 95.7 95.6 | 94.9 96.8 | 0.3 0.4 | 0.3 0.5 |
| 1 month 3 months 25° C. | 96.1 95.6 | 95.1 96.1 | 0.9 0.9 | 0.7 1.0 |
| 1 month 3 months 30° C./75% r.h. | 95.7 95.2 | 94.5 95.1 | 1.4 2.7 | 1.5 2.9 |
| 1 month 3 months | 95.2 95.7 | 94.7 94.5 | 1.5 3.1 | 1.9 3.9 | r.h. = relative humidity

Residual Solvents:

Preparation and lyophilization of compound 1 liposomes led to methanol levels below 0.1%. No chloroform was detectable (limit=0.05%).

f) Vesicle Size

Vesicle sizes of liposomes usually are determined by laser light scattering and are expressed as mean hydrodynamic diameter, as long as particle size distribution is approximately unimodal. Mean diameters of compound 1 liposomes are about 200–300 nm after manufacture and filtration through 0.2 μm membranes. Vesicle size is smaller (150–250 nm) after freeze drying and re-dispersion in water. During storage vesicles are getting smaller again: a 10% decrease after 3 months is observed (Table 5):

TABLE 5

Particle size of compound 1 liposomes after lyophilization, storage and reconstitution

| Batch | Hydr. Radius | | Hydr. Diameter | Distribution [∅ (nm)] | |
| --- | --- | --- | --- | --- | --- |
|  | Rh (nm) | PDC % | Dh (nm) | min. | max. |
| 2 initial | 111.5 | 50 | 223 | 147 | 500 |
| 1 month, 5° C. | 96.8 | 48 | 194 | 126 | 434 |
| 3 months, 5° C. | 99.3 | 49 | 199 | 132 | 454 |
| 1 initial | 108 | 47 | 216 | 140 | 546 |
| 1 month, 5° C. | 93.2 | 48 | 186 | 120 | 468 |
| 3 months, 5° C. | 95.3 | 49 | 191 | 124 | 498 |

Dh = hydrodynamic diameter
PDC = polydispersity coefficient
Rh = hydrodynamic radius

TABLE 6.1

Lyophilization of compound 1 liposomes

| Cryoprotectant | Eutectic temperature | Appearance |
| --- | --- | --- |
| Sucrose | −30 | white, compact, some minor fissures |
| Trehalose | −28 | white, compact, smooth surface |
| Lactose | −28 | white, compact, smooth surface |
| Mannitol | −30 | white, compact, detachment of single discs |
| Maltose | −27 | white, compact, ruptured edge |
| no sugar | — | porous, cracked |
| Fructose | −36 | white, compact, rough surface |
| Glucose | −38 | white, small pores |
| Galactose | −36 | white, small pores |
| Mannose | −37 | unhomogeneous |
| Xylitol | −38 | unhomogeneous |
| Sorbitol | −33 | white, porous |

TABLE 6.2

Particle size of compound 1 liposomes: effects of lyophilization

| Cryoprotectant | Particle Size [mean diameter (nm) ± SD (n = 3)] | | |
| --- | --- | --- | --- |
|  | before lyophilization (b) | after lyophilization (a) | Quotient (a/b) |
| Sucrose | 597 (±174) | 205 (±29) | 0.3 (±0.1) |
| Trehalose | 407 (±58) | 250 (±35) | 0.6 (±0.1) |
| Lactose | 381 (±52) | 217 (±19) | 0.6 (±0.1) |
| Mannitol | 224 (±15) | 187 (±12) | 0.8 (±0.1) |
| Maltose | 209 (±8) | 188 (±16) | 0.9 (±0.1) |
| no sugar | 274 (±15) | 338 (±15) | 1.2 (±0.1) |
| Glucose | 377 (±60) | 200 (±32) | 0.5 (±0.2) |
| Galactose | 391 (±15) | 265 (±60) | 0.7 (±0.1) |
| Fructose | 304 (±40) | 241 (±30) | 0.8 (±0.1) |
| Mannose | 398 (±50) | 331 (±30) | 0.8 (±0.1) |
| Xylit | 320 (±4) | 250 (±16) | 0.8 (±0.1) |
| Sorbit | 373 (±57) | 139 (±10) | 0.4 (±0.1) |

Compound 1 liposomes were prepared with concentration of:
compound 1 = 1.5 mg/ml
soy-bean lecithins = 15 mg/ml
cryoprotectants = 4% h) IR/ATR Spectroscopy

Ex situ experiments were carried out on multi-bilayer membranes with a compound 1/lipid ratio of 1:2 and without use of a buffer containing high concentrations of electrolytes. In these liposomes the stoichiometric ratio of compound 1 to lipids was experimentally confirmed, i.e. a homogenous distribution of drug substance and phospholipids is maintained in the bilayer membranes. An unexpected finding was that compound 1 although used in the base form is protonated when incorporated in the lipid membrane.

Based on the experimentally determined dichroitic ratios the angle between the axis of the compound 1 molecule and the perpendicular line to the membrane plane was analyzed. With high probability compound 1 is located in parallel to the hydrocarbon chains of the lipids and with a deviation of 0°–30° C. from the perpendicular line. The orientations of compound 1 and of POPC are illustrated by computer modeling in FIG. 2.

i) HPLC Analysis

Drug loading, i.e. concentration of compound 1 per ml of liposomes was determined by HPLC: Spheri-5 RP 18 columns were from Brownlee Labs; Pump, U.V.-detector and Auto sampler from Kontron. The mobile phase was acetonitrile/water/triethylamine (800/200/1). Care had to be taken on the sample preparation before application on the columns: neutral liposomes (no charge) are physically unstable. Thus aggregation and sedimentation can be prevented by diluting the samples 1:1 with methanol 50%.

EXAMPLE 2

Preparation of Liposomes
(Compound 1; Phase Transition Temperature Above Room Temperature)

Liposomes having a phase transition temperature (Tc) above room temperature are prepared as described in Example 1 but using distearoyl-PC (DSPC) and distearoyl-PG (DSPG) instead of PC and DMPG. In a further variant DSPC and DSPG are replaced by hydrogenated phosphatidyl choline (HPC). The hydration, homogenization and filtration steps are done at temperatures above Tc. Comparable results are obtained as described in Example 1.

EXAMPLE 3

Biological Effects of Liposomes Against Candidiasis
(Compound 1; in vivo, Systemic Candidiasis)

Compound 1 liposomes (POPC/PS, 7:3 w/w) were examined in a murine model of deep fungal infection against systemic candidiasis: Mice (Balb/C) are infected by intravenous route with Candida albicans NRB at a concentration of $4 \times 10^5$ cells via the tail vein. Two i.v. treatments are given on days 3 and 4 after infection with 0.5 mg of liposomal compound 1 per kg. Survival is observed until day 21. Organ candida counts are determined in liver and kidney.

Surprisingly, 10 out of 20 animals survived to day 21. All control infected but untreated animals died by day 8. Thus at the low dose of 0.5 mg/kg survival of 50% of the animals is prolonged from 9 to at least 21 days in the Candida model.

Organ Candida counts were determined in liver and kidney of mice treated with liposomal compound 1 at days 5 and 10 after infection.

The result is indicated in Table 7:

TABLE 7

| Organ Candida counts in liver and kidney | | |
|---|---|---|
| Day | Liver | Kidney |
| 5 | 160 ± 74 | 302 ± 68 |
| 10 | 62 ± 32 | 126 ± 93 |

A marked reduction at day 10 is seen.

An alternative test is as decribed above but to use Candida at a concentration $5 \times 10^5$ cells. The liposomes are administered on days 1, 3 and 5.

EXAMPLE 4

Preparation of Liposomes (Compound 1; Large Scale)

Liposomes with the same composition as mentioned under Examples 1 and 2 above are prepared with the one-step preparation method of M. Brandl et al. (*Dreg Dev. and Ind. Pharm.* 16 [1990] 2167) using Superdispax homogenization followed by microfluidizer treatment. According to this process one liter of a 20 mM phosphate buffer, pH 6.5, containing 4.5% of lactose is homogenized in a Superdispax homogenizer. 35 g of PC, 15 g of DMPG and 5 g of compound 1 are dispersed in the solution at the maximal dispersion rate (15.000 RPM) until after 0.5 hours a mean particle size of 200 nm is obtained. Then the liposomes are transferred into a Mircofluidizer and further homogenized. This procedure reduces the particle size of the liposomes to 90+10 nm.

When HPC and DSPG are used instead of PC and DMPG in the above example, and the temperature in the process is raised up to 70° C., then liposomes are obtained having a mean particle size of 135 nm.

EXAMPLE 5

Preparation of Liposomal Gel (Compound 1)

2 g of compound 1 (free base form) are solubilized, together with 20 g of soybean phosphatidyl choline (PC), 4 g of cholesterol and 0.2 g of α-tocopherol in 10 g of propylene glycol at 50° (organic solution A). Organic solution A is allowed to cool down to 25°. 62 g of a 20 mM isotonic phosphate buffer pH 6.5 solution is stirred in a Superdispax homogenizer and 0.2 g methyl p-hydroxybenzoate, 0.02 g propyl p-hydroxybenzoate and 0.15 g Na-EDTA are solubilized in it (aqueous solution B). Aqueous solution B is mixed at a speed of 3000 rpm. Then organic solution A is introduced into the stirred aqueous solution at a speed of 1.0 ml/min. Liposomes with a particle size of less than 1000 nm are formed. At reduced speed 0.5 g hydroxy propyl methyl cellulose is added to the liposomal suspension to form a gel. The gel can be filled into tubes.

EXAMPLE 6

Pulmonal Application With Nebulizer (Compound 1)

The experiment is conducted employing a Twin Impinger device as described in Hallworth et al.,*J. Pharm. Pharma* 39 966–972 (1987) as Type 11 Twin Impinger and under the term "Glass Impinger" in the *British Pharmacopoeia* 1988, 11, Appendix XVII C (A204–A207). A liposome suspension containing compound 1 in base form with phospholipid composition PC (10.5 mg/ml) and DMPG (4.5 mg/ml) and a liposome suspension containing compound 1 in base form with phospholipid composition H (hydrogenated) (HPC) (10.5 mg/ml PBSL) and DSPG (4.5 mg/ml PBSL), both with a mean particle size between 100 nm and 200 nm, are nebulized and are led into the Twin Impinger with an air flow of 60 l/min for 30 min. The quantities recovered from each part of the Twin Impinger are measured using spectrophotometry. Results show that there is no significant difference between the distributions of the liposome suspensions with a different phospholipid composition (and with a different transition temperature). In both cases more than 50% is recovered from the lower impinger chamber, corresponding to high delivery to the alveoli (see FIG. 3).

Influence of Nebulization on Particle Size:

In order to study the effects of the nebulization on the size of liposomes with different phospholipid compositions and different transition temperatures, the suspensions are nebulized using a "Pari Inhalation Standard Gerät". The above described liposome compositions are used, however having a mean particle size of above 500 nm. Samples are taken at various times from the container of the nebulizer and are measured using laser light scattering. It appears that the size of the liposomes decreases in both cases rapidly within 10 minutes and reaches a size of about 150 nm to 200 nm after 12 minutes (FIG. 4).

Subsequently the mean size of the liposomes which are leaving the nebulizer are measured using laser light scattering. It appears that all the liposomes which leave the nebulizer have a mean size approximately between 90 nm and 140 nm.

It can be concluded that the liposomes of both compositions which are aerosolized are small and that the particle size does not relate directly to the particle size of the liposomes which are introduced into the container of the nebulizer. Surprisingly, the size of the MLV's in the gel state (HPC/DSPC) is reduced as rapidly as the size of the MLV's (PC/DMPC) in liquid state, although nebulization takes place at room temperature, far below the gel-to-liquid state phase transition temperature of the liposomes in gel state.

EXAMPLE 7

Biological Effects of Liposomes Against Aspergillosis

The biological efficacy of the two liposomes variants as obtained from Example 4 as herein before described are examined in a murine model of pulmonal fungal infection against aspergillosis with cortisone induced immune suppression: Twenty gram ICR female mice are treated for three days with 2.5 mg of cortisone acetate subcutaneously beginning one day prior to challenge to produce immune suppression. The mice are intranasally challenged with $1.25\times10^6$ spores of Aspergillus fumigatus-ATCC 13073 suspended in 60 microliters of saline with Tween 80 while under light pentobarbital anesthesia. Liposome treatment is begun five days prior to challenge and continued every other day for eleven treatments. Chemotherapy is accomplished using the nose only exposure to nebulized liposomes for 30 minutes per day. Each experimental group consists of 15 animals including non-challenged/non-treated, challenged/non-treated and challenged/placebo treated controls. Evaluation of the test is done twenty days after challenge by determining the survival rates and body weights of the tested animals.

Applied daily dosages of the liposomes of the compound of formula I of e.g. from 0.01 to 1 mg per kg prolonges survival of the treated mice or an improvement of the disease condition of the aspergillosis can be observed.

This test method is based on a murine model of pulmonary aspergillosis as described by S. Allen et al. at the 9th International Symposium on Future Trends in Chemotherapy, Geneva, Switzerland (1990), in "Aerosol Amphotericine B Chemotherapy in an Immune Compromised Murine Model".

Liposomal preparations containing liposomes of the invention exhibit pharmacological activity and therefore are useful as pharmaceuticals.

In particular, they are useful in the treatment of systemic fungal infections. This activity appears e.g. in mice systemically infected with Candida upon administration of the liposomes of the invention at a dosage of from about 0.1 mg/kg to about 2 mg/kg of liposomal compound of formula I, e.g. as described in Example 3.

For the above indication the appropriate dosage will, of course, vary depending upon, for example, the form of the compound used, the host, the mode of administration and the nature and severity of the condition being treated. However, in general, satisfactory results in animals are indicated to be obtained at daily dosages of from about 1 μg/kg to about 10 mg/kg, especially 0.05 mg/kg to 1 mg/kg, or e.g. 0.1 to 1 mg/kg animal body weight of compound of formula I in liposomal form. In larger mammals, for example humans, an indicated daily dosage is in the range of from about 0.1 mg to about 500 mg of a compound of formula I in liposomal form, conveniently administered, for example, in divided doses up to four times a day. Preferably the daily dosage is from about 5 mg to about 50 mg of the compound of formula I per day.

Further in particular, the liposomal preparations are useful for the treatment of pulmonal fungal infections. This activity appears e.g. in mice pulmonarily infected with Aspergillus upon administration of the liposomes of the invention by inhaling a nebulized liposomal preparation for 30 minutes per day, e.g. as described in example 7.

For the above indication the appropriate dosage will, of course, vary depending upon, for example, the host and the nature and severity of the condition being treated. However in general, satisfactory results in animals are indicated to be obtained at daily treatments with the nebulized liposomal form of the compound of formula I with inhaled doses from about 0.1 mg/kg to about 10 mg/kg animal body weight. In larger mammals, for example humans, an indicated daily dosage is in the range from about 10 mg to about 1000 mg per day, conveniently administered, for example, in divided doses up to four times a day. Preferred daily dosages are from about 20 mg to about 400 mg, e.g. from about 100 mg to about 200 mg per day.

Further in particular, the liposomal preparations are useful for the topical treatment of fungal infections of the skin. The most suitable applications forms are gels, creams and lotions containing the liposomal preparations of the compound of formula I, e.g. the liposomal gel as prepared according to example 5, e.g. for the same indications as known for other topical compositions, e.g. fungal infections and in the same dosages, e.g. as confirmed by standard clinical trials. Typical effective dosages are achieved when the active agent concentration in the treated skin tissue is between 10 and 10'000 ng per square centimeter. Preferred skin tissue concentrations are between 500 and 2000 ng per square centimeter e.g. 1000 ng per square centimeter e.g. as indicated by standard pharmacological tests. However higher and lower dosages may be effective and may be determined by standard tests. For example the effective concentrations in the treated skin may be achieved when applying e.g. the compound of formula I in form e.g. a 2% liposomal gel according to the invention over the infected area, e.g. 5 mg active agent per day to a skin area of about 100 square centimeters.

Administration may be peroral, topical or parenteral. It preferably is topical or parenteral, especially parenteral, particularly pulmonal.

Parenteral administration preferably is in the form of a suspension in a pharmaceutically acceptable solution such as a sterile isotonic aqueous solution. Such solutions may be obtained fully prepared or may be prepared from preformed components.

Peroral administration preferably involves encapsulated liposomes whereby the liposomes are protected from most gastric and intestinal digestion before release from liposomes.

Topical administration is effected with liposomal preparations such as lotions, gels, creams or ointments. Local administration may also be effected by the inhalation route, especially to the lung, e.g. using a suitable nebulizer or spray device. Nebulization of liposomal suspensions can be performed with a standard nebulizer operated with compressed air or ultrasonication, although other methods of nebulization may be employed, e.g. pressurized dose aerosols or dry powder formulations by appropriate devices. The liposome suspension can also be dried by lyophilization or spray drying and the obtained powder can be suspended in an appropriate propellant such as a fluorochlorohydrocarbon or inhaled with a powder-inhaler device. If the compound of formula I is encapsulated in liposomes then a localized action can be obtained in the respiratory tract avoiding systemic adverse reactions.

Such preparations may be manufactured in conventional manner. Unit dosage forms contain, for example, from about 0.025 mg to about 250 mg of a compound of formula I in liposomal form.

The invention also provides a method for the treatment of systemic fungal infections comprising administering a pharmaceutically effective amount of a liposomes comprising as the active agent a compound of formula I as defined above to a subject in need of such treatment.

What is claimed is:

1. A topical pharmaceutical composition comprising the compound of formula I

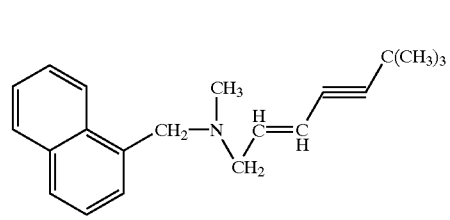

in free base form or acid addition salt form, encapsulated in liposomes, which composition contains phospholipid components which are selected from 1)palmitoyl-oleyl-phosphatidyl-choline, 2)dioleoyl-phosphatidyl-glycerol, 3)dioleoyl-phosphatidyl-serine, 4)a mixture of palmitoyl-oleyl-phosphatidyl-choline and palmitoyl-oleyl-phosphatidyl-glycerol, 5)dimyristoyl-phosphatidyl-choline, or 6) a mixture of dimyristoyl-phosphatidyl-choline and dimyristoyl-phosphatidyl-glycerol, said composition further comprising phosphatidylethanolamine-polyethyleneglycol.

* * * * *